United States Patent [19]

Lim

[11] 4,352,883

[45] Oct. 5, 1982

[54] ENCAPSULATION OF BIOLOGICAL MATERIAL

[75] Inventor: Franklin Lim, Richmond, Va.

[73] Assignee: Damon Corporation, Needham Heights, Mass.

[21] Appl. No.: 24,600

[22] Filed: Mar. 28, 1979

Related U.S. Application Data

[63] Continuation-in-part of Ser. No. 953,413, Oct. 23, 1978, abandoned.

[51] Int. Cl.³ .................. C12N 11/10; C12N 11/04; C12N 5/00
[52] U.S. Cl. .................................. 435/178; 3/1; 264/4; 424/34; 424/35; 424/94; 435/1; 435/175; 435/182; 435/240
[58] Field of Search .............. 435/1, 182, 188, 262, 435/174, 175, 177, 178, 240; 424/31, 32, 34, 94, 101, 106, 110, 178; 264/4; 252/316; 3/1

[56] References Cited

U.S. PATENT DOCUMENTS

| | | | |
|---|---|---|---|
| 3,522,346 | 7/1970 | Chang | 435/188 X |
| 3,725,113 | 4/1973 | Chang | 424/101 X |
| 3,730,841 | 5/1973 | Forgione et al. | 435/182 |
| 3,733,205 | 5/1973 | Shorers et al. | 435/262 X |
| 3,827,565 | 8/1974 | Matsumora | 435/182 X |
| 3,860,490 | 1/1975 | Guttag | 435/182 |

FOREIGN PATENT DOCUMENTS

1600988 9/1970 France .

OTHER PUBLICATIONS

Chang, T.M.S., Biomedical Applications of Immobilized Enzymes and Proteins, vol. I, Plenum Press, N.Y., 1977, (pp. 69–90 and 147–153).
Tze, et al., Implantable Artificial Endocrine Pancreas Unit Used to Restore Normoglycaemia in the Diabetic Rat, Nature, vol. 264, 1976, (pp. 466–467).

*Primary Examiner*—David M. Naff
*Attorney, Agent, or Firm*—Kenway & Jenney

[57] ABSTRACT

A core material such as living tissue, individual cells, hormones, enzymes or antibodies is encapsulated in a semipermeable membrane that is permeable to small molecules for contact with the core material but is impermeable to potentially deleterious large molecules. Encapsulation may be carried out by suspending the core material in an aqueous medium containing a water soluble gum that can be reversibly gelled, forming the suspension into droplets, contacting the droplets with a solution of multivalent cations to gel the droplets as discrete, shape-retaining, water insoluble temporary capsules and cross-linking a surface layer of the temporary capsules to produce a semipermeable membrane around the capsules. Optionally the gel within the membrane may be reliquified by removing multivalent cations from the gel.

22 Claims, 1 Drawing Figure

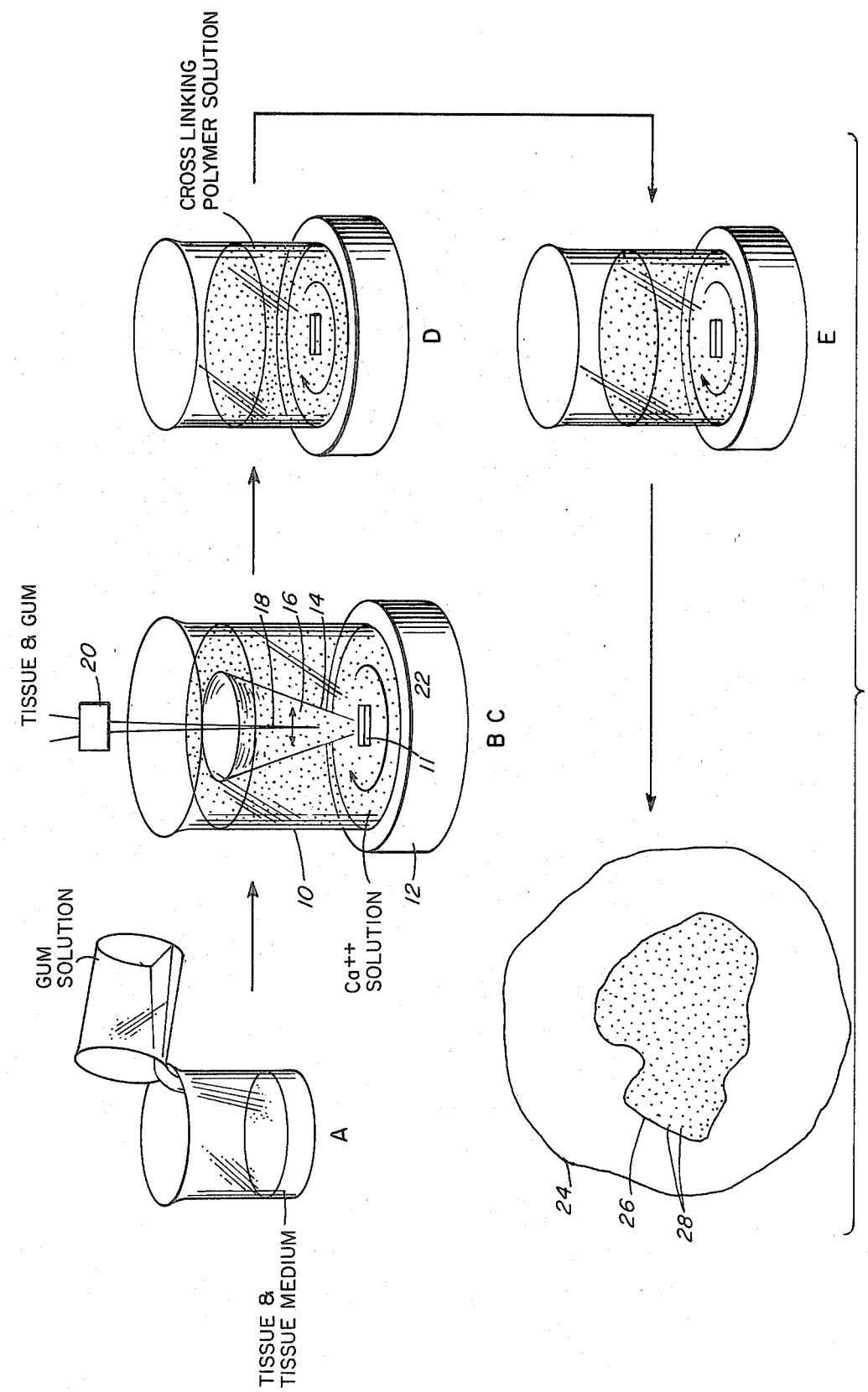

ENCAPSULATION OF BIOLOGICAL MATERIAL

REFERENCE TO RELATED APPLICATION

This application is a continuation-in-part of copending U.S. application Ser. No. 953,413, filed Oct. 23, 1978, now abandoned, the disclosure of which is incorporated by reference herein.

BACKGROUND OF THE INVENTION

This invention relates to a process for encapsulating tissue or individual cells so that they remain viable and in a protected state within a membrane which is permeable to nutrients, ions, oxygen, and other materials needed to both maintain the tissue and support its normal metabolic functions, but impermeable to bacteria, lymphocytes, and large proteins of the type responsible for immuochemical reactions resulting in rejection. The process enables the production of, for example, an insulin producing system or other hormone producing system as it allows encapsulation of mammalian pancreatic beta cells, alpha cells, intact islets of Langerhans, and other tissues or tissue fractions which secrete hormones. The capsules may be suspended in a culture medium and will excrete hormone over an extended period. The capsules may also be used as an artificial pancreas which can be implanted, e.g., by injection, into a diabetic mammal and will function in vivo to excrete insulin and other hormones in response to ambient sugar concentration.

it is believed that the art is devoid of methods for encapsulating living tissue such that the tissue remains viable. Attempts to accomplish this are frustrated by the conditions required for capsular membrane formation which are typically hostile to living systems. Copending U.S. application Ser. No. 606,166, to F. Lim et al., filed Aug. 20, 1975, the disclosure of which is incorporated herein by reference, discloses a technique for encapsulating labile biological materials within a semipermeable membrane. This technique is capable, for example, of encapsulating enzymes within a membrane from which the enzyme cannot escape, while allowing free passage of the enzyme's substrate. However, while the technique involves reaction conditions which preserve the fragile operability of biological materials, no suggestion is made that living tissue can be encapsulated.

Encapsulated live cells, organelles, or tissue have many potential uses. For example, within a semipermeable membrane, the encapsulated living material can be preserved in a permanent sterile environment and can be shielded from direct contact with large, potentially destructive molecular species, yet will allow free passage of lower molecular weight tissue nutrients and metabolic products. Thus, the development of such an encapsulation technique could lead to systems for producing useful hormones such as insulin. In such systems, the mammalian tissue responsible for the production of the material would be encapsulated in a manner to allow free passage of nutrients and metabolic products across the membrane, yet prohibit the passage of bacteria. If membrane permeability could be controlled, it is possible that this approach could also lead to artificial organs which could be implanted in a mammalian body, e.g., a diabetic, without rejection and with controlled hormone release, e.g., insulin release triggered by glucose concentration.

Various attempts have been made to produce artificial organs suitable for implantation in mammalian bodies by providing a mechanical semipermeable barrier, e.g., a Millipore diffusion chamber or a capillary tube chamber, about tissue excised from a donor. Such artificial organs normally require surgical implantation. Furthermore, the protective mechanisms of mammalian bodies isolate the implant, typically by plugging pores by fibroblastic overgrowth.

SUMMARY OF THE INVENTION

In one aspect, the instant invention provides a method of encapsulating core material such as living tissue, individual cells, or biologically active materials in a semipermeable membrane. The basic approach involves suspending the tissue to be encapsulated in a physiologically compatible medium containing a water soluble substance that can be made insoluble in water, that is, gelled, to provide a temporary protective environment for the tissue. The medium is next formed into droplets containing the tissue and gelled, for example, by changing conditions of temperature, pH, or ionic environment. The "temporary capsules" thereby produced are then subjected to a treatment, which can be a known treatment, that results in the production of membranes of a controlled permeability (including impermeability) about the shape-retaining temporary capsules.

The temporary capsules can be fabricated from any nontoxic, water soluble substance that can be gelled to form a shape retaining mass by a change of conditions in the medium in which it is placed, and also comprises plural groups which are readily ionized to form anionic or cationic groups. The presence of such groups in the polymer enables surface layers of the capsule to be cross-linked to produce a "permanent" membrane when exposed to polymers containing multiple functionalities of the opposite charge.

The presently preferred material for forming the temporary capsules is polysaccharide gums, either natural or synthetic, of the type which can be (a) gelled to form a shape retaining mass by being exposed to a change in conditions such as a pH change or by being exposed to multivalent cations such as $Ca^{++}$; and (b) permanently "crosslinked" or hardened by polymers containing reactive groups such as amine or imine groups which can react with acidic polysaccharide constituents. The presently preferred gum is alkali metal alginate. Other water soluble gums which may be used include guar gum, gum arabic, carrageenan, pectin, tragacanth gum, xanthan gum or acidic fractions thereof. When encapsulating thermally refractory materials, gelatin or agar may be used in place of the gums.

The preferred method of formation of the droplets is to force the gum-nutrient-tissue suspension through a vibrating capillary tube placed within the center of the vortex created by rapidly stirring a solution of a multivalent cation. Droplets ejected from the tip of the capillary immediately contact the solution and gel as spheroidal shaped bodies.

The preferred method of forming a permanent semipermeable membrane about the temporary capsules is to "crosslink" surface layers of a gelled gum of the type having free acid groups with polymers containing acid reactive groups such as amine or imine groups. This is typically done in a dilute solution of the selected polymer. Generally, the lower the molecular weight of the polymer, the greater the penetration into the surface of the temporary capsule, and the greater the penetration, the less permeable the resulting membrane. Permanent crosslinks are produced as a consequence of salt formation between the acid reactive groups of the crosslinking polymer and the acid groups of the polysaccharide gum. Within limits, semipermeability can be controlled by setting the molecular weight of the crosslinking polymer, its concentration, and the duration of reaction. Crosslinking polymers which have been used with success include polyethylenimine and polylysine. Molecular weight can vary, depending on the degree of permeability required, between about 3,000 and 100,000 or more. Good results have been obtained using polymers having an average molecular weight on the order of 35,000.

The capsules can be engineered to have a selected in vivo useful life by astute selection of the cross-linking polymer. Proteins or polypeptide crosslinkers, e.g., polylysine, are readily attached in vivo resulting in relatively rapid destruction of the membrane. Cross-linkers not readily digestible in mammalian bodies, e.g., polyethyleneimine, result in longer lasting membranes. By selecting the crosslinking polymer or by cross-linking simultaneously or sequentially with two or more such materials, it is possible to preselect the length of time the implanted tissue remains protected.

Optionally, with certain materials used to form the temporary capsules, it is possible to improve mass transfer within the capsule after formation of the permanent membrane by re-establishing the conditions under which the material is liquid, e.g., removing the multivalent cation. This can be done by ion exchange, e.g., immersion in phosphate buffered saline or citrate buffer. In some situations, such as where it is desired to preserve the encapsulated tissue, or where the temporary gelled capsule is permeable, it may be preferable to leave the encapsulated gum in the crosslinked, gelled state.

An alternative method of membrane formation involves an interfacial polycondensation of polyaddition similar to the procedure disclosed in U.S. application Ser. No. 606,166. This approach involves preparing a suspension of temporary capsules in an aqueous solution of the water soluble reactant of a pair of complementary monomers which can form a polymer. Thereafter, the aqueous phase is suspended in a hydrophobic liquid in which the complementary reactant is soluble. When the second reactant is added to the two-phase system, polymerization takes place at the interface. Permeability can be controlled by controlling the makeup of the hydrophobic solvent and the concentration of the reactants. Still another way to form a semipermeable membrane is to include a quantity of protein in the temporary capsule which can thereafter be crosslinked in surface layers by exposure to a solution of a crosslinking agent such as gluteraldehyde.

The foregoing process has been used to encapsulate viable Islets of Langerhans which, in a medium containing the nutrients and other materials necessary to maintain viability and support in vitro metabolism of the tissue, excrete insulin in the presence of glucose. Encapsulated tissue has been maintained in a viable state for three months. Also, liver cells have been encapsulated and have been demonstrated to be in a physiologically active state.

In another aspect, the instant invention provides a tissue implantation method which does not require surgery and which overcomes many of the problems of immune rejection. In accordance with the invention, the capsules are injected into a suitable site in a mammalian body, and function normally until the tissue expires, or until natural body processes succeed in isolating the capsules so that substances required for viability of the tissue are no longer available. At this point, because surgery is not required for the implant, fresh tissue may be readily provided by another injection. The mammalian body may accordingly be provided with the specialized function of the tissue as long as desired.

In a preferred embodiment of the invention, mammalian Islets of Langerhans, or islet preparations containing selected amounts of alpha, beta, and/or delta cells from islets are encapsulated in polylysine and polyethyleneimine cross-linked alginate membranes. These may be periodically injected, e.g., into the peritoneal cavity of a diabetic mammalian body and function as an artificial pancreas.

Accordingly, it is a primary object of the invention to provide a method of encapsulating living cells, organelles, or tissue in a membrane permeable to the nutrients and other substances needed for maintenance and metabolism and to metabolic products, but impermeable to bacteria and to substances having a molecular weight above a selected level, so as to exclude agents responsible for immunological rejection of the foreign tissue. Other objects of the invention include the provision of encapsulated living tissue useful for producing hormones such as insulin and for effecting complex chemical changes characteristic of the in vivo tissue, to provide an insulin generation system, to provide a body fluid detoxifying system, and to provide encapsulated activated charcoal.

Other objects of the invention are to provide a method of implanting living tissue in mammalian bodies and to provide a non-surgical tissue implantation technique. Still another object is to provide a method of encapsulating living tissue which allows the production of capsules having a high surface area to volume ratio and membranes with a preselected in vivo residence time. Another object of the invention is to provide an artificial pancreas.

These and other objects and features of the invention will be apparent from the following description of some preferred embodiments and from the drawing.

BRIEF DESCRIPTION OF THE DRAWING

The sole FIGURE of the drawing schematically illustrates a preferred method of encapsulating living tissue suitable for use in the process of the invention, and the product microcapsule.

DESCRIPTION OF THE PREFERRED EMBODIMENT

The tissue, organelle, or cell to be encapsulated is prepared in accordance with well-known prior art techniques in finely divided form and suspended in an aqueous medium suitable for maintenance and for supporting the ongoing metabolic processes of the particular tissue involved. Media suitable for this purpose are available commercially. The average diameter of the material to be encapsulated can vary widely between less than a micron to several millimeters. Mammalian islets of Langerhans are typically 140 to 200 microns in diameter. Of course, individual cells such as pancreatic beta cells, alpha cells, delta cells, or various ratios thereof, whole islet of Langerhans, individual hepatocytes, organelles, or other tissue units may be encapsulated as desired. Also, microorganisms may be encapsulated as well as non-living materials such as biological materials.

The ongoing viability of such living matter is dependent, inter alia, on the availability of required nutrients, oxygen transfer, absence of toxic substances in the medium, and the pH of the medium. Heretofore, it has not been possible to maintain such living matter in a physiologically compatible environment while simultaneously encapsulating. The problem has been that the conditions required for membrane formation have been lethal or harmful to the tissue, and no method of membrane formation which tissue can survive in a healthy state has been forthcoming. It has now been discovered that certain water soluble substances which are physiologically compatible with living tissue and can be rendered water insoluble to form a shape-retaining, coherent mass can be used to form a "temporary capsule" or protective barrier layer about tissue particles. Such a material is added, typically at low concentration, to the tissue culture medium. The solution is then formed into droplets containing tissue together with its maintenance medium and is immediately rendered water insoluble and gelled, at least in a surface layer. Thereafter, the shape-retaining temporary capsules are provided with a permanent semipermeable membrane. Where the material used to form the temporary capsules permits, the capsule interior may be reliquified after formation of the permanent membrane. This is done by re-establishing the conditions in the medium at which the material is soluble.

The material used to form the temporary capsules may be any non-toxic, water-soluble material which, by a change in the surrounding temperature, pH, or ionic environment or concentration, can be converted to a shape retaining mass. Preferably, the material also contains plural, easily ionized groups, e.g., carboxyl or amino groups, which can react by salt formation with polymers containing plural groups which ionize to form species of opposite charge. As will be explained below, this type of material enables the deposition of a permanent membrane of a selected porosity and a selected in vivo lifespan in surface layers of the temporary capsule.

The presently preferred materials for forming the temporary capsule are water-soluble, natural or synthetic polysaccharide gums. Many such materials are commercially available. They are typically extracted from vegetable matter and are often used as additives to various foods. Sodium alginate is the presently preferred water soluble gum. Other usable gums include guar gum, gum arabic, charageenan, pectin, tragacanth gum, xanthan gum, or their acidic fractions.

These materials comprise glycoside-linked saccharide chains. Many contain free acid groups, which are often present in the alkali metal ion form, e.g., sodium form. If a multivalent ion such as calcium or strontium is exchanged for the alkali metal ion, the liquid, water-soluble polysaccharide molecules are "crosslinked" to form a water insoluble, shape-retaining gel which can be resolubilized on removal of the ions by ion exchange or via a sequestering agent. While essentially any multivalent ion which can form a salt is operable, it is preferred that physiologically compatible ions, e.g., calcium, be employed. This tends to preserve the tissue in the living state. Other multivalent cations can be used for less fragile material.

Other gums can be switched between the water soluble and gelled, water insoluble state simply by changing the pH of the medium in which they are dissolved.

A typical tissue-tissue medium-gum solution composition comprises equal volumes of tissue in its medium and a one to two percent solution of gum in physiological saline. When employing sodium alginate, a 1.0 to 1.5 percent solution has been used with success.

When encapsulating materials which can resist changes in temperature, gelatin or agar may be used to form the temporary capsules. These can be gelled by injection into a low temperature environment. Other water soluble substances such as hydroxyethyl methacrylate may also be used.

In the next step of the encapsulation process, the gum solution containing the tissue is formed into droplets of a desired size. Thereafter, the droplets are immediately gelled to form shape-retaining spherical or spheroidal masses. Apparatus for conducting these latter steps is illustrated at step BC of the drawing. A beaker 10 containing an aqueous solution of multivalent cation, e.g., 1.5 percent $CaCl_2$ solution, is fitted with a magnetic stirring bar 11 and stirrer 12. The stirring mechanism is actuated to produce a vortex 14 having a hollow center 16. A capillary tube 18 of a selected inside diameter is positioned within hollow region 16 of the vortex and fitted with a vibrator 20. The suspension containing tissue and the solubilized gum is fed through the capillary. The effect of surface tension which would induce the formation of relatively large droplets is minimized by the vibrator so that droplets, illustrated at 22, of a size comparable to the inside diameter of the capillary, are shaken off of the capillary tip. These immediately contact the solution where they absorb calcium ions. This results in "crosslinking" of the gel and in the formation of a shape-retaining, high viscosity protective temporary capsule containing the suspended tissue and its medium. The capsules collect in the solution as a separate phase and are separated by aspiration.

In an alternative embodiment of the process, a small amount of polymer of the type used for permanently crosslinking the gum is included in the solution together with the multivalent ions (or other solution capable of gelling the particular gum employed). This results in the formation of permanent crosslinks. Capsules of this type have certain advantages if the goal is to preserve the tissue.

In the next step of the process, a semipermeable membrane is deposited about the surface of the temporary capsules. There are a variety of methods available for effecting this step, some of which are known in the art. For example, interfacial polymerization techniques can be exploited. In interfacial polymerization, a pair of at least difunctional mutually reactive monomers, or a monomer and a relatively low molecular weight polymer, one of which is soluble in polar solents such as water and the other of which is soluble in hydrophobic solvents such as hexane, are caused to react at the interface of an emulsion of the water-in-oil type. In accordance with the procedure disclosed in the Lim et al application noted above, the material to be encapsulated is suspended or dissolved in water together with the water soluble component of the reaction, the aqueous phase is emulsified in a hydrophobic solvent, and the complementary monomer is added to the continuous phase of the system so that polymerization occurs about the aqueous droplets. By controlling the nature of the continuous phase solvent and the concentration of the reactant contained therein, it is possible to exercise control over pore size and to produce semipermeable microcapsules.

This technique may be used in accordance with the instant invention if the water soluble reactant is dissolved in an aqueous solution, and the solution is used to suspend the temporary capsules. This liquid suspension is then emulsified in, for example, hexane, or a hexane-chloroform mix. The complementary monomer is next added, preferably incrementally, to induce interfacial polymerization at the surface of the aqueous droplets. Because of the gelled mass of polysaccharide surrounding the suspended tissue, and especially if suitably buffered polyfunctional amino-group containing polymers such as certain proteins are employed as the water-soluble reactant, the process is such that the tissue survives the encapsulation in a healthy condition. The substances useful in forming membranes with the polyfunctional amines include diacids, diacid halides, and multifunctional sulfonyl halides. In addition to the polyamines, diamines, polyols, and diols may be used. Molecules containing plural amine groups may also be crosslinked with glutaraldehyde to form a membrane. Another useful method of membrane formation is by interfacial polymerization utilizing polyaddition reactions. In this case, for example, multifunctional amines absorbed in surface layers of the temporary capsules are reacted with epichlorohydrin, epoxidized polyesters, or diisocyanate.

The preferred method of forming the membrane, illustrated as step D in the drawing, is to permanently cross link surface layers of the droplets by subjecting them to an aqueous solution of a polymer containing groups reactive with functionalities in the gel molecules. Certain long chain quaternary ammonium salts may be used for this purpose in some circumstances. When acidic gums are used, polymers containing acid reactive groups such as polyethylenimine and polylysine may be used. In this situation, the polysaccharides are crosslinked by interaction between the carboxyl groups and the amine groups. Advantageously, permeability can be controlled by selecting the molecular weight of the crosslinking polymer used. For example, a solution of polymer having a low molecular weight, in a given time period, will penetrate further into the temporary capsules then will a high molecular weight polymer. The degree of penetration of the crosslinker has been correlated with the resulting permeability. In general, the higher the molecular weight and the less penetration, the larger the pore size. Broadly, polymers within the molecular weight range of 3,000 to 100,000 daltons or greater may be used, depending on the duration of the reaction, the concentration of the polymer solution, and the degree of permeability desired. One successful set of reaction conditions, using polylysine of average molecular weight of about 35,000 daltons, involved reaction for two minutes, with stirring, of a physiological saline solution containing 0.0167 percent polylysine. Optimal reaction conditions suitable for controlling permeability in a given system can readily be determined empirically without the excercise of invention.

The selection of the cross-linker(s) also determines the in vivo residence time of the capsules. In the system described above, the permanent capsule membrane comprises polysaccharide (a readily injestible substance), cross-linked with either or both a polypeptide or protein, e.g., polylysine, or a synthetic substance, e.g., polyethyleneimine. Polymers vary with respect to the rate at which they can be dispersed in vivo. Some are digested without difficulty, e.g., protein; others are slowly degraded, and still others remain indefinitely. The process of the invention contemplates cross-linking with one or more polymers to produce capsules having a selected rate of dissolution in vivo, ranging generally between a few hours or days to substantial permanence. The example which follows discloses how to produce capsules which remain intact at least about two months within the peritoneal cavity of rats. However, the invention is not limited to these particular capsule membranes nor to capsules of this degree of in vivo life. In fact, the optimal in vivo life of the microcapsules depends upon the their intended use and their site of implantation. Those skilled in the art will be able to produce microcapsules of a selected in vivo lifespan empirically without the exercise of invention in view of this disclosure.

At this point in the encapsulation, capsules may be collected which comprise a permanent semipermeable membrane surrounding a gelled solution of gum, tissue compatible culture medium, and tissue particles. If the object is simply to preserve the tissue in a protective environment, no further steps need be done. However, if mass transfer is to be promoted within the capsules and across the membranes, it is preferred to reliquify the gel to its water soluble form. This may be done by reestablishing the conditions under which the gum is a liquid, e.g., changing the pH of the medium or removing the calcium or other multifunctional cations used. In the gels which are insoluble in the presence of multivalent cations, the medium in the capsule can be resolubilized simply by immersing the capsules in phosphate buffered saline, which contains alkali metal ions and hydrogen ions. Monovalent ions exchange with the calcium or other multifunctional ions within the gum when, as shown at stage E of the drawing, the capsules are immersed in the solution with stirring. Other salts, e.g. sodium citrate, may be used for the same purpose.

Lastly, depending on the type of semipermeable membrane formation technique employed, it may be desirable to treat the capsules so as to tie up free amino groups or the like which would otherwise impart to the capsules a tendency to clump. This can be done, for example, by immersing the capsules in a solution of sodium alginate.

The invention contemplates the injection of encapsulated, finely divided tissue, multicellular fractions thereof, or individual cells into an appropriate site within a mammalian body for the purpose of providing the body, at least temporarily, with the tissue's specialized physiological function. The procedure has the dual advantages of obviating the need for surgical implantation (although capsules may be implanted surgically if desired) and successfully dealing with the problems of immune rejection and natural physical isolation. Preferably, the capsule membranes consist of substances which are injested after expiration of the tissue. As noted above, this can be accomplished by employing a cross-linker which resists in vivo breakdown so that a given useful in vivo life is attained.

From the foregoing it will be apparent that the encapsulation process and implantation technique of the invention can be practised using a wide variety of reagents and encapsulated materials and can be varied significantly without departing from the scope and spirit of the invention. The following example should accordingly be construed in all respects as illustrative and not in a limiting sense.

EXAMPLE 1

Islets of Langerhans were obtained from rat pancreas and added to a complete tissue culture (CMRL-1969 Connaught Laboratories, Toronto, Canada) at a concentration of approximately $10^3$ islets per milliliter. The tissue culture contains all nutrients needed for continued viability of the islets as well as the amino acids employed by the Beta cells for making insulin. Four-tenths of a milliliter of the islet suspension was then added to a one-half milliliter volume of 1.2 percent sodium alginate (Sigma Chemical Company) in physiological saline.

Next, 80 milliliters of a 1.5 percent calcium chloride solution were placed in a 150 milliliter beaker on a stirrer and stirred at a rate which induced the formation of a vortex having a conical-shaped void at its center. A glass capillary having a gradually decreasing diameter ending in a tip of inside diameter about 300 microns was then fitted with a vibrator (60 cycles per second). The capillary tip was then placed within the center of the vortex, the vibrator turned on, and the sodium alginate-culture medium-tissue suspension was forced therethrough with an infusion pump. Droplets on the order of 300-400 microns in diameter are thrown from the tip of the capillary and immediately enter the calcium solution.

After 10 minutes, the stirrer was turned off and the supernatant solution was removed by aspiration. The gelled capsules were then transferred to a beaker containing 15 ml of a solution comprising one part of a 2% 2 (cyclohexylamino) ethane sulfonic acid solution in 0.6% NaCl (isotonic, ph=8.2) diluted with 20 parts 1% $CaCl_2$. After a 3 minute immersion, the capsules were washed twice in 1% $CaCl_2$.

The capsules were then transferred to a 32 ml solution comprising 1/80 of one percent polylysine (average MW 35,000 AMU) in physiological saline. After 3 minutes, the polylysine solution was decanted. The capsules were then washed with 1% $CaCl_2$, and then suspended for 3 minutes in a solution of polyethyleneimine (MW 40,000-60,000) produced by diluting a stock 3.3% polyethyleneimine solution in morpholino propane sulfonic acid buffer (0.2 M, pH=6) with sufficient 1% $CaCl_2$ to result in a final polymer concentration of 0.12%. The resulting capsules, having permanent semipermeable membranes, are then washed twice with 1% $CaCl_2$, twice with physiological saline, and mixed with 10 ml of a 0.12 percent alginic acid solution.

The capsules resist clumping, and many can be seen to contain islets of Langerhans. Gel on the interior of the capsules is reliquified by immersing the capsules in a mixture of saline and citrate buffer (pH=7.4) for 5 minutes. Lastly, the capsules are suspended in CMLR-69 medium.

Under the microscope, these capsules have an appearance illustrated in the drawing. They comprise a very thin membrane 24 which encircle an islet 26 within which individual cells 28 can be seen. Molecules having a molecular weight up to about 100 thousand can traverse membrane 24. This allows oxygen, amino acids, nutrients, and plasma components used in culture media (e.g., fetal calf plasma components) to reach the islet and allows insulin to be excreted.

EXAMPLE 2

After repeated washings in physiological saline, microcapsules made in accordance with Example 1 containing approximately 15 islets were suspended in 3 milliliters of CMRL-1969. When eight days old, in the presence of 600 mg/dl glucose, the capsules excreted, in one run, 67 microunits/ml insulin in 1.5 hours. In a second run, 68 microunits/ml insulin were produced in the same amount of time. One week old capsules, in the same medium, but in the presence of 100 mg/dl glucose, in a first run, excreted 25 $\mu$units/ml insulin in 1.2 hours, and in a second run, excreted 10 $\mu$units/ml.

EXAMPLE 3

Diabetic rats with blood gluclose levels in the range of 500-700 mg/dl were each treated with approximately $10^3$ islets encapsulated as set forth in Example 1, and suspended in physiological saline. The capsules were introduced by injection into the peritoneal cavity using a number 19 needle fitted to a syringe. Blood sugar levels were assayed daily and uniformly found to be below 300 mg/dl. Animals sacrificed after two months showed no signs of toxic reaction about the site of the implantation. Capsules removed from sacrificed animals after a two-month in vivo life were intact and showed no signs of degradation.

EXAMPLE 4: ENCAPSULATION OF HEPATOCYTES

The procedure of example 1 was repeated except that 0.5 ml of a liver cell suspension in Hank's solution was used in place of the 0.4 ml islet suspension. The ongoing viability of the liver tissue has been demonstrated by the dye exclusion technique (trypan blue exclusion). It is known that liver tissue, in vitro, can ingest toxins from its environment. Accordingly, toxins of a molecular weight low enough to pass through the semipermeable membranes are injested and destroyed by the tissue. Essentially all toxins treated by the liver are low molecular weight materials. However, the toxins may be protein-complexed. Capsular permeability can be varied according to the need.

EXAMPLE 5

The procedure of example 1 is repeated except that particulate activated charcoal is suspended directly in the sodium alginate solution, the half milliliter of tissue suspension is omitted, and polylysine of an average molecular weight of 35,000 is used as a crosslinker. As long as the charcoal particles are smaller than the smallest inside diameter of the capillary used to produce the droplets, charcoal of high surface area surrounded by a semipermeable membrane results. These effectively prohibit the escape of charcoal chips or dust, yet can be used to absorb medium range molecular weight materials (up to about 2,000 daltons) from fluid passed about the capsules.

The operability of the process has been demonstrated with other living cells including red blood cells, using serum as a medium, sperm cells, using semen as the medium, and baker's yeast. Those skilled in the art will appreciate that a variety of other materials can be encapsulated in addition to thoese specifically set forth herein, and that permeability can be controlled as desired for selected applications of the process. Accordingly, other embodiments are within the following claims.

What is claimed is:

1. A process for encapsulating viable tissue within a semipermeable membrane, said process comprising the steps of:

A. suspending finely divided living tissue in an aqueous medium which is physiologically compatible with the tissue and which contains a water soluble substance which
   (a) is physiologically compatible with the tissue; and
   (b) can be reversibly gelled to form a coherent, shape-retaining mass;
B. forming the suspension into droplets of a size sufficient to envelop tissue;
C. gelling the droplets to form discrete, shape-retaining temporary capsules;
D. forming a permanent semipermeable membrane about the temporary capsules; and
E. reliquifying the gel within the membrane.

2. A process for encapsulating a core material within a semipermeable membrane, said process comprising the steps of:
A. placing the material in a solution of a water-soluble substance that can be reversibly gelled;
B. forming the solution into droplets;
C. gelling the droplets to produce discrete shape-retaining temporary capsules;
D. forming semipermeable membranes about the temporary capsules; and
E. reliquifying the gel within said membranes.

3. The process of claim 2 wherein said substance comprises a gum.

4. The process of claim 3 wherein said gum has free acid groups and said membrane formation step is effected by contacting the temporary capsules with a polymer of a molecular weight between 3000 and 100,000 daltons and having free amino groups, said contacting being effective to form permanent polymer crosslinks between acid groups in a surface layer of the capsule.

5. The process of claim 4 wherein the polymer used for crosslinking is selected from the group consisting of polylysine and polyethylenimine, said polymer having an average molecular weight of about 35,000 daltons.

6. The process of claim 2 wherein the membrane is formed by an interfacial polymerization wherein the temporary capsules are used as a core material in the aqueous phase of a water-in-oil emulsion.

7. The process of claim 6 wherein the reactants used in the polymerizatiion are selected from the group consisting of water soluble polyols, diols, polyamines, and diamines, and water immiscible diacid halides, diacids, and multifunctional sulfonyl halides.

8. The process of claim 6 wherein the interfacial polymerization is a polyaddition reaction.

9. The process of claim 2 wherein the material is selected from the group consisting of enzymes, immunoproteins, activated charcoal particles, and viable tissue.

10. The process of claim 3 wherein the gum is an alkali metal alginate.

11. The process of claim 3 wherein the gum comprises a polysaccharide containing free acid groups.

12. The process of claim 2 wherein said core material is selected from the group consisting of hormones, enzymes and antibodies.

13. A process for encapsulating a core material within a membrane permeable to proteins of a molecular weight no greater than about 100 thousand daltons, said process comprising the steps of:
A. suspending the core material in an aqueous medium which contains a water-soluble gum containing acid groups;
B. forming the suspension into droplets;
C. subjecting the droplets to a solution of multivalent, cations to gel the droplets as discrete, shape-retaining, water insoluble temporary capsules; and
D. permanently cross-linking surface layers of said temporary capsules to produce a semipermeable membrane about said droplets by subjecting them to a polymer containing substitutents reactive with the acid groups of said gum, said polymer having a molecular weight within the range of 3000-100,000 daltons.

14. The process of claim 13 comprising the additional step of resolubilizing the gel within said capsules.

15. The process of claim 13 wherein the water soluble gum is sodium alginate and multivalent cation solution is a calcium solution.

16. The process of claim 15 including the additional step of removing the calcium ions contained within said capsules to resolubilize the gelled alginate interior of the membranes of said capsules.

17. The process of claim 15 wherein said core material is a mammalian tissue selected from the group consisting of Islets of Langerhans, liver, and individual cells thereof and said medium is a physiologically compatible tissue medium.

18. The process of claim 13 wherein said core material is a mammalian tissue selected from the group consisting of Islets of Langerhans, liver, and individual cells thereof and said medium is a physiologically compatible tissue medium.

19. The process of claim 13 wherein said core material comprises living tissue and said aqueous medium is a complete tissue culture medium sufficient to maintain said tissue in vitro.

20. The process of claim 13 wherein said cross-linking polymer is selected from the group consisting of polylysine and and polyethylenimine.

21. The process of claim 20 wherein the average molecular weight of said polymer is about 35,000 daltons.

22. The process of claim 13 wherein said forming step is effected by forcing droplets of the suspension through a capillary tube while vibrating the tube within the center of a vortex formed by imparting circular fluid motion to an aqueous solution containing multi-valent cations.

* * * * *